(12) United States Patent
Brown

(10) Patent No.: US 6,223,133 B1
(45) Date of Patent: Apr. 24, 2001

(54) METHOD FOR OPTIMIZING MULTIVARIATE CALIBRATIONS

(75) Inventor: James M. Brown, Flemington, NJ (US)

(73) Assignee: Exxon Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/312,727

(22) Filed: May 14, 1999

(51) Int. Cl.⁷ ..................................................... G01N 31/00
(52) U.S. Cl. .......................... 702/85; 702/28; 250/339.12
(58) Field of Search ................. 702/85, 22–23, 702/28, 30, 49; 250/339.09, 339.11, 339.12

(56) References Cited

U.S. PATENT DOCUMENTS

| | | | |
|---|---|---|---|
| 5,121,337 | * 6/1992 | Brown | 702/28 |
| 5,435,309 | * 7/1995 | Thomas et al. | 250/339.12 |
| 5,459,677 | * 10/1995 | Kowalski et al. | 702/28 |
| 5,699,269 | * 12/1997 | Ashe et al. | 702/30 |
| 5,892,228 | * 4/1999 | Cooper et al. | 250/339.12 |

* cited by examiner

Primary Examiner—Marc S. Hoff
Assistant Examiner—Bryan Bui
(74) Attorney, Agent, or Firm—Ronald D. Hantman

(57) ABSTRACT

The present invention is a method for optimizing multivariate calibrations such as those used on FT-IR analyzers. The method involves the selection of an optimum subset of samples to use in the calibration from a larger set of available samples. The subset selection is done so as to minimize the bias of the resulting calibration while simultaneously maintaining acceptable standard errors and ensuring maximal range for the model.

31 Claims, No Drawings

METHOD FOR OPTIMIZING MULTIVARIATE CALIBRATIONS

BACKGROUND OF THE PRESENT INVENTION

The present invention relates to multivariate models. In particular, the present invention relates to calibrating multivariate models. More particularly, the present invention relates to optimizing the calibration of multivariate models.

Multivariate models are used to relate multivariate analytical measurements such as infrared spectra (independent X-block variables) to component concentrations and physical properties (dependent Y-Block variables). During the calibration of these models, data (spectra and concentrations/properties) are measured for a set of calibration samples, and a regression model is built to relate the dependent Y-Block variables to the independent X-Block variables. One means of performing such a calibration is through the use of Constrained Principal Spectra Analysis (J. M. Brown, U.S. Pat. No. 5,121,337, Jun. 9, 1992). Alternatively, Principal Component Regression (PCR), Partial Least Squares Regression (PLS), or Multilinear Regression (MLR) could also be used. PCR, PLS and MLR are described in ASTM Practice E1655. Once the multivariate model is calibrated, it may be applied to new sample X-Block data to estimate the corresponding concentration/property Y-Block data for the unknown.

Multivariate models are the basis by which on-line infrared analyzers are used to estimate component concentrations such as benzene content, saturates content, aromatics content and olefin content for motor gasolines, diesel fuels, jet fuels and process streams, and properties such as research and motor octane number of gasolines and cetane number for diesel fuels from infrared spectra. For example, Maggard describes the use of MLR and PLS models for measuring paraffin, isoparaffin, aromatics, naphthene and olefin (PIANO) contents of motor gasolines and gasoline components (U.S. Pat. No. 5,349,189, Sep. 20, 1994). Maggard also describes the use of MLR for measuring octane and cetane numbers (U.S. Pat. No. 4,963,745, Oct. 16, 1990 and U.S. Pat. No. 5,349,188, Sep. 20, 1994). Perry and Brown (U.S. Pat. No. 5,817,517, Oct. 6, 1998.) describe the use of FT-IR for determining the composition of feeds to hydrocarbon conversion, separation and blending processes.

The use of multivariate models is not limited to infrared analyzers. Jaffe describes the use of Gas Chromotography and MLR to estimate octane numbers for gasolines (U.S. Pat. No. 4,251,870, Feb. 17, 1981). Ashe, Roussis, Fedora, Felsky and Fitzgerald describe the use of Gas Chromotography/Mass Spectrometery (GC/MS) and PCR or PLS multivariate modeling for predicting chemical or physical properties of crude oils (U.S. Pat. No. 5,699,269, Dec. 16, 1997). Cooper, Bledsoe, Wise, Sumner and Welch describe the use of Raman spectroscopy and PLS multivariate modeling to estimate octane numbers and Reid vapor pressures of gasolines (U.S. Pat. No. 5,892,228, Apr. 06, 1999).

The accuracy of a multivariate model is highly dependent on the samples that are used in its calibration. If the samples do not span a sufficient range of the potential variation in the X-Block data, then many of the unknowns that are analyzed will be outliers relative to the model. Since analysis of outliers is via extrapolation of the model, the accuracy of the estimates may be diminished. In addition, if the calibration samples do not adequately represent the structure of the X- and Y-Blocks, the resultant models may produce biased estimates of the component concentration and property values. The present invention is aimed at minimizing this potential bias while simultaneously ensuring that the X-Block range is adequately spanned by the calibration set.

In developing applications that use multivariate models, it is typical to first conduct a feasibility study to demonstrate that the component concentrations and/or properties can be related to the multivariate analytical measurement in question (e.g. infrared spectrum). Since for such feasibility studies, only a limited amount of data is collected, initial models will typically be generated using all available data and using cross-validation as a means of estimating model performance. As additional materials are analyzed, they can be added to the model to improve the scope of the multivariate model. Gethner, Todd and Brown (U.S. Pat. No. 5,446,681, Aug. 29, 1995) describe how samples which extend the range of the calibration or fill voids in the calibration might be automatically identified and captured.

As more samples become available, it is typical to divide the available samples into a calibration set which is used to develop the multivariate model, and a validation set which is used to validate the performance of said model. ASTM Standard Practice E1655 describes the use of calibration and validation sets. If samples are taken from a process, it is typical that samples near the production average may become over-represented in the data set relative to samples representing more atypical production. If the division between calibration and validation sets is made randomly, extreme samples (outliers) may end up in the validation set where they are estimated via extrapolation of the resultant model, and the range of the model may be limited. In addition, the over-representation of the more average production may lead to biased estimates for samples away from this average.

Several methods have been proposed to make the subdivision of samples into calibration and validation set based on the independent variable X-Block data, which in the case of FT-IR analyzers are the infrared spectra.

Honigs, D. E., Hieftje, G. M. Mark, H. L. and Hirschfeld, T. B. (*Analytical Chemistry*, 1985, 57, 2299–2303) proposed a method for selecting calibration samples based on the use of spectral subtraction. The spectrum with the largest absorption is initially selected, and subtracted from all other spectra to cancel absorptions at the frequency of the largest absorption. The spectrum with the largest absolute value signal remaining is selected next, and again subtracted from all other spectra to cancel the signals at the frequency of the largest absolute value signal. The process is repeated until the remaining signal is judged to be at the spectral noise level. For each independent signal in the X-Block data, the selection of one calibration sample cancels the signal. Thus this selection process can only select a very limited number of samples before reaching the noise level. The resultant calibration set would contain too few samples relative to the rank of the data matrix to be useful for modeling. Further, since the selection process does not make use of the dependent (Y-Block) variable s, it may not produce unbiased models.

Kennard, R. W. and Stone, L. A. (*Technometrics* 1969, 11, 13 7–149) proposed a subset selection method which was applied to the problem of calibration set selection by Bouveresse, E., Harmn C., Massart, D. L., Last, I. R., and Prebble, K. A. (*Analytical Chemistry* 1996, 68, 982–990). Distances were calculated between spectra based on the raw spectral data. The two samples that were farthest apart were selected as calibration sample s. For each remaining sample, minimum distance to a calibration sample is calculated. The sample with the largest nearest neighbor distance is added to the calibration set, and the process is repeated until the desired number of calibration samples is obtained. Isaksson, Tomas & Naes, Tormod (*Applied Spectroscopy* 1990, 44, 1152–1158) used a similar sample selection procedure based on cluster analysis of sample spectra. A Principal Component Analysis of the sample spectra is conducted, and the furthest neighbors are calculated in the variable space defined by the scores for the Principal Components with the largest eigenvalues. Neither selection process makes use of the dependent (Y-Block) variables, and neither is guaranteed to produce unbiased models.

To include Y-Block information in the sample selection process, the following methodology has been used. A list of the samples is sorted based on one of the property/component concentrations to be modeled. Every $m^{th}$ sample in the list is marked as a calibration sample. The samples are resorted on successive property/component concentrations, and the marking procedure is repeated. The samples marked as designated as calibration samples. The value of m is chosen such that the desired number of calibration samples is selected. The procedure ensures that the samples span the range of the Y-Block. As an alternative, the scores from a Principal Components Analysis (or Constrained Principal Spectra Analysis) of the X-Block data can be included in this procedure to ensure that the calibration samples span both the X- and Y-Blocks. This methodology tends to minimize outliers in the validation set, but it has not been found to produce optimum, unbiased models.

SUMMARY OF THE INVENTION

The present invention is a method for optimizing multivariate calibrations such as those used on FT-IR analyzers. The method involves the selection of an optimum subset of samples to use in the calibration from a larger set of available samples. The subset selection is done so as to minimize the bias of the resulting calibration while simultaneously maintaining acceptable standard errors and ensuring maximal range for the model. The optimization procedure consists of the following steps: (1) The multivariate analytical data and property/composition data for a set of available samples is divided in to calibration and validation subsets; (2) a model is calculated that relates the multivariate analytical data to the property/composition data for the calibration subset; (3) the model is used to calculate property/composition data for the validation subset from the validation set multivariate analytical data; (4) For each property being modeled, a standard error of calibration, a standard error of validation, and a validation bias are calculated, and a determination is made as to whether samples in the validation set are outliers relative to the calibration; (5) A fitness function is calculated from the two standard errors, the bias, and the number of outliers; (6) The division of the samples into calibration and validation subsets is varied to minimize the fitness function. The minimization can be done using a Genetic Algorithm, although other optimization methods could potentially be used.

Selection of samples to use in the calibration of multivariate models is critical to the accuracy of the models. Various methods have been suggested for this purpose, essentially all of which make the selections based solely on spanning the range of the independent variables used in the calibration model. For example as discussed above, Honigs, D. E., Hieftje, G. M. Mark, H. L. and Hirschfeld, T. B. (*Analytical Chemistry*, 1985, 57, 2299–2303) proposed a method for selecting calibration samples based on the use of spectral subtraction. Isaksson, Tomas & Naes, Tormod (*Applied Spectroscopy* 1990, 44, 1152–1158) proposed a sample selection procedure based on cluster analysis of sample spectra. Kennard, R. W. and Stone, L. A. (*Technometrics* 1969, 11, 137–149) proposed a method for selecting calibration samples based on distances between sample spectra. These methods will typically select the most unique samples in the set of available samples for inclusion in the calibration, but since they do not make use of the dependent variables in making the selection, they do not guarantee unbiased models. The present invention makes use of both independent and dependent variables in making the selection so as to produced unbiased calibrations.

DESCRIPTION OF THE PREFERRED EMBODIMENT

If the matrix X contains multivariate analytical data such as infrared spectra as columns, and the vector y contains component concentrations such as benzene, olefins or aromatics content or properly data such as specific gravity or octane numbers, then the calculation of a multivariate model involves the determination of a prediction vector p that relates X to y, $$y = X^t p \quad [1]$$

ASTM Practice E1655 discusses how the multivariate model is developed using either Multivariate Linear Regression (MLR), Partial Least Squares (PLS), or Principal Components Regression (PCR). The current invention preferably uses models developed using Constrained Principal Spectra Analysis (CPSA—J. M. Brown, U.S. Pat. No. 5,121,337, Jun. 9, 1992), but could use MLR, PLS or PCR as well. Using CPSA, the calibration spectra are first orthogonalized to correction vectors that represent signals that arise from the measurement process itself. Such signals could include, but are not limited to baseline variations and spectrometer purge contaminant spectra. The orthogonalized spectra form the columns of a matrix X'. The singular value decomposition of X' is calculated as $$X' = USV^t \quad [2]$$

The first k Principal Components corresponding to the signals in X' are retained, and the remaining Principal Components are discarded. The concentration/property data is regressed against the Principal Component scores to obtain regression coefficients, $$y = Vb \Rightarrow \hat{b} = V^t y \quad [3]$$

The prediction vector is calculated as $$\hat{p} = US^{-1}\hat{b} \quad [4]$$

If $x_u$ is a vector representing the spectrum of an unknown sample after orthogonalilation relative to the correction vectors, then the estimation of the concentration property data can be made directly using the estimated prediction vector $$\hat{y} = x\hat{p} \quad [5]$$

Alternatively, the scores for the unknown may be estimated as $$V_u = x_u US^{-1} \quad [6]$$

and the property/composition estimate can be made using the regression coefficients $$\hat{y} = v_u \hat{b} \quad [7]$$

The calculation of the multivariate model thus involves either the calculation of the regression coefficients, $\hat{b}$, or the calculation of the prediction vector, $\hat{p}$. Typically, for PCR and CPSA, the independent model variables are the Principal Component Scores which are regressed against the dependent variable property/composition data in calculating regression coefficients, $\hat{b}$. Similarly for PLS, the independent model variables are the latent variable scores. For MLR, the independent model variables may be the measured analytical data, as for instance the infrared absorption at selected frequencies, or a mathematical function of this data as in a second derivative spectrum. For MLR, the model calculation involves inverting the X matrix to calculate the prediction vector, $\hat{p}$.

If X represents the matrix containing all available spectra as columns, then it is desirable to subdivide X into two matrices, $X_{cal}$, which contains the calibration set, and $X_{val}$ which contains a validation set. X may be the raw spectra as in the case of MLR, PCR or PLS, or it may contain preprocessed, for example orthogonalized, spectra as in the case of CPSA. The objective of the current invention is to make the subdivision of the samples in X into the calibration and validation sets such that there are no outliers (samples analyzed via extrapolation) in the validation set, the property/component concentration estimates for the validation set are unbiased, and the standard errors for the calibration and validation are maintained at acceptable levels. Alternatively, instead of subdividing X, a scores matrix, V, may be calculated from X using equation [2], and the scores matrix may be subdivided into calibration and validation subsets.

In its most basic implementation, the current invention involves subdividing the available multivariate analytical data, X, into two subsets, $X_{cal}$ and $X_{val}$, and similarly subdividing the property/composition data vector y into $y_{cal}$ and $y_{val}$. A multivariate model is calculated using $X_{cal}$ and $y_{cal}$. A singular value decomposition of $X_{cal}$ is calculated using equation [2]. The scores for the calibration set, $V_{cal}$, are regressed against the property/composition data, $y_{cal}$, to calculate the regression coefficients, $\hat{b}$. The model is used to calculate estimates of the properties for the calibration set, $\hat{y}_{cal}$ using equation [7]. Scores for the validation set, $V_{val}$, are then calculated using equation [6], and property estimates for the validation set, $\hat{y}_{val}$, are made using equation [7]. The standard deviation of the property data is calculated as:

$$StdY = \sqrt{\frac{y^t y}{n-1}} \qquad [8]$$

The Standard Error of Calibration is calculated as:

$$SEC = \sqrt{\frac{(\hat{y}_{cal} - y_{cal})^t (\hat{y}_{cal} - y_{cal})}{n_{cal} - k}} \qquad [9]$$

The Standard Error of Validation is calculated as:

$$SEV = \sqrt{\frac{(\hat{y}_{val} - y_{val})^t (\hat{y}_{val} - y_{val})}{n_{val}}} \qquad [10]$$

The Validation Bias (VB) is calculated as the average difference between the estimate, $\hat{y}_{val}$, and $y_{val}$. A t value is calculated as:

$$t = \frac{\sqrt{n_{val}} \, VB}{SEV} \qquad [11]$$

A Mahalanobis Distance is calculated for each sample in the calibration set.

$$MD_{cal} = \text{diagonal}(V_{cal}(V_{cal}^t V_{cal})^{-1} V_{cal}^t) \qquad [12]$$

Similarly, Mahalanobis Distances are calculated for each sample in the validation set.

$$MD_{val} = \text{diagonal}(V_{val}(V_{cal}^t V_{cal})^{-1} V_{val}^t) \qquad [13]$$

The maximum value for $MD_{cal}$ is determined, and the number of validation samples, $n_{outliers}$, with $MD_{val}$ greater than the maximum for the calibration are counted. A Fitness Function, FF, is calculated as:

$$FF = (1 + n_{outliers})\left(t + \sqrt{n_{cal}} \frac{SEC}{StdY} + \sqrt{n_{val}} \frac{SEV}{StdY}\right) \qquad [14]$$

The subdivision of X into $X_{cal}$ and $X_{val}$ is varied to minimize FF. Once and acceptable minimum is found, the samples corresponding to the multivariate analytical data in $X_{cal}$ are used to calibrate the model, and those corresponding $X_{val}$ are used to validate the model.

If multiple multivariate models based on the same set of X-Block data (spectra) but different Y-Block (property/component concentration) data are to be optimized, the Fitness Functions in [14] are calculated for each individual property/component concentration and are summed to obtain the FF used in the Genetic Algorithm optimization.

Since the above described implementation of the invention involved repetitive singular value decompositions of the various permutations of $X_{cal}$, it can be computer intensive, and thus time consuming if X contains a large number of samples, frequencies or both. A preferred, and less computer intensive implementation of the invention avoids this problem. The singular value decomposition of the entire X matrix is first calculated using equation [2]. The scores matrix, V is then subdivided into two parts, $V_{cal}$ and $V_{val}$, and the y vector is divided similarly into $y_{cal}$ and $y_{val}$. Regression coefficients for the model, $\hat{b}$, are calculated by applying [3] to $V_{cal}$ and $\hat{y}_{cal}$. Estimates $\hat{y}_{cal}$ and $\hat{y}_{val}$ are then calculated using [7]. The subdivision of V into $V_{cal}$ and $V_{val}$ is varied to minimize FF. Once an acceptable minimum is found, the samples corresponding to $V_{cal}$ are used to calibrate the multivariate model, and those corresponding to $V_{val}$ are used to validate the model.

If samples are to be added to an existing model to extend the range of the model, than a slightly different implementation of the invention is used. If $X_{model}$ contains the spectra for the existing model, and $y_{model}$ contains the corresponding property data, then $V_{model}$ are the corresponding scores obtained from the singular value composition of $X_{model}$. The model is used to analyze the spectra of the additional samples that are not in the model, $X_{new}$. The scores for these additional samples, $V_{new}$ are calculated using equation [6]. The scores for the original model, $V_{model}$, and those for the additional samples, $V_{new}$, are combined into one V matrix. Similarly, the property/composition data for the model samples, $y_{model}$, and for the additional samples, $y_{new}$, are combined into one y vector. V and y are then subdivided into $V_{cal}$ and $V_{val}$ and $y_{cal}$ and $y_{val}$ and the optimization proceeds as described above.

The fitness function described here is only an example of one that can be used for the invention. Other fitness functions can be used to implement the invention, but all will typically include a measure of the number of samples in the validation set which are predicted via extrapolation (outliers), a measure of the prediction error for the calibration and validation sets, and a measure of the bias for the validation set. For example, another suitable fitness function for optimization is given by:

$$FF = (1 + n_{outliers})\left(t + \sqrt{n_{cal}}\frac{SEC}{R} + \sqrt{n_{val}}\frac{SEV}{R}\right) \quad [15]$$

where R, the reproducibility of the reference method used to generate the property/composition data has replaced StdY in [14].

A Genetic Algorithm is used to locate an acceptable minimum in FF. Shaffer, R. E. and Small, G. W. (*Analytical Chemistry* 1997, 69, 236A–242A) have reviewed Genetic Algorithms. Shaffer, R. E., Small, G. W., and Arnold, M. A. (*Analytical Chemistry* 1996, 68, 2663–2675) employed Genetic Algorithms to optimize the position and width of a digital filter which was coupled to a PLS model for analysis of glucose in biological matrices by Near-Infrared. Paradkar, R. P.; and Williams, R. R. (*Applied Spectroscopy*, 1997, 51 92–99) used Genetic Algorithms to select wavelengths for Multilinear Regression modeling. None of these references suggest the use of Genetic Algorithms for the optimization of the subdivision of samples into calibration and validation sets. The use of the Genetic Algorithms follows the following steps:

1. Initiation—An initial set of parent vectors, generation 1, is generated. Each vector consists of n values that are set to 1 if a sample is in the calibration set, and to 0 (or −1) if the sample is in the validation set. Typically the assignment of the n values to 1 and 0 (or −1) is done randomly with the constraint that the number of samples in each set must be in an acceptable range. For instance, the number of 1s in the vector may be constrained to be within the range from 0.4 n to 0.6 n. The number of parent vectors is the size of a generation. Typically 40–80 parent vectors have been found to give acceptable performance, but other numbers of parent vectors could potentially work as well or better. If preexisting models are to be used as starting points, one or more of the initial parent vectors may be set to correspond to the samples in these models.
2. Evaluation—the Fitness Function, FF, is calculated for each of the parent vectors.
3. Selection of the fittest—Roulette or Binary Tournament selection is used to select mating parents from the initial set. For Binary Tournament selection, pairs of potential parents are randomly selected, and the parent with the lower FF is allowed to mate. For Roulette selection, the sum of 1/FF is calculated for all the parents in the initial set. Each initial parent is assigned to a fraction of the range from 0–1 corresponding to its 1/FF value divided by this sum. A random number generator is used to select parents for mating. Parents with a lower FF value have a proportionately larger fraction of the range from 0–1 and thus are more likely to be selected for mating. The number of total parents selected is equal to the number in the initial set, and individual parents may appear multiple times.
4. Recombination—A random number generator is used to determine if each pair of mating parents will exchange information. If the random number is less than a preset probability level (typically 0.95), then exchange will occur. A second random number generator is used to determine where along the vectors the exchange will occur. If the original parent vectors are n elements long, and the random number generator indicates exchange should occur at element i, then the first child vector will contain elements 1 to i from parent 1, and elements i+1 to n from parent 2. Similarly, the second child will contain elements 1 to i from parent 2, and elements i+1 to n from parent 1.
5. Mutation—After recombination, a random number generator is used to determine if mutation of each child will occur. If the random number is less than a preset probability level (typically 0.2 to 0.25), then mutation will occur. A second random number generator is used to determine where along the child vector the mutation will occur. If the mutation is to occur at element j, and element j is initially 1, then element j will be set to 0 (or −1). Similarly, if element j is initially 0 (or −1), then it will be set to 1.
6. The Fitness Functions for this new generation, the children from steps 4 and 5, are determined. The vectors with the best (lowest) Fitness Functions are stored. If no stop criterion has been reached, then steps 3–6 are repeated for the new population. Stop criteria include:

Reaching a predetermined number of generations (typically 40–100);

Having no change in some fixed percentage of the best vectors for some fixed number of generations. Typically, if the 25% of the population with the lowest Fitness Functions do not change for 3 successive generations, the process has converged sufficiently.

The Genetic Algorithm routine used in the examples below used 1 if a sample was in the calibration set, and −1 is the sample was in the validation set. The use of 1, −1 allows the uniqueness of children to be more easily checked within the software in which the GA routine was written. More standard GA routines would use 1 and 0.

The Genetic Algorithm calculations may be repeated several times to try to locate the optimum model, particularly if the first stop criteria (reaching predetermined number of generations) is reached. The starting populations for each calculation can be random, or based on some fraction of the best vectors from previous calculations. Since Genetic Algorithms can get stuck in local minima, multiple runs starting from different populations are more likely to find the global minimum. However, since the local minima may in themselves be adequate subsets for producing unbiased models, the repetition of the Genetic Algorithm may be used, but is not required by the current invention.

EXAMPLE 1

Optimization of an FT-MIR Multivariate Model for Estimation of Benzene and Aromatics Contents of Motor Gasolines The initial X-Block data consists of a set of 149 FT-MIR spectra of motor gasolines collected at 2 $cm^{-1}$ resolution over the 7000–400 $cm^{-1}$ spectral region. A CPSA model is initially build using data in the 4750–3140 $cm^{-1}$ and the 2220–1630 $cm^{-1}$ regions. Orthogonalization to cubic and quadratic baseline polynomials is used in the two regions to minimize effects of baseline variation. Orthogonalization to water vapor spectra is used to minimize sensitivity to spectrometer purge variation. An initial model was build using all 149 spectra, and 9 Constrained Principal Components. Two Y-Block vectors were used in the modeling, benzene content and aromatics content. Data for these Y-Block vectors was obtained using ASTM D5580. Aromatics contents for the 149 samples ranged from 17.6 to 28.6 volume %, and the benzene contents from 0.23 to 0.94 volume %. The Standard Errors of Calibration for this initial fill set model were 0.342 for aromatics content, and 0.032 for benzene content.

The scores from this initial model were used as the X-Block inputs to the Genetic Algorithm. The benzene content and aromatics content Y-Block vectors were used in the optimization. Data for 5 samples which were found to be Studentized T outliers for either aromatics or benzene content were removed from the X-and Y-Blocks prior to optimization, but were included in the data used to calculate validation statistics for the final models.

For applying the Genetic Algorithm optimization, the number of calibration samples was constrained to fall between 72 and 102. Each generation consisted of 100 vectors, and up to 50 generations were calculated. A 95% probability of recombination and a 25% probability of mutation were used. The Genetic Algorithm optimization was initiated twice from random initial populations. For each of these random starts, the Genetic Algorithm was restarted 3 additional times using the best 25 vectors from the previous pass as one fourth of the initial population. The vector with the lowest Fitness Funtion was used to determine the division of sample spectra between calibration and validation sets. The results for the model build on the segregated sets are shown in Table 1. The model is unbiased for both components, and the weighted average of the standard errors of calibration and validation are comparable to or better than the SEC for the model based on all 149 spectra. The maximum Mahalanobis distance for the validation set is less than that for the calibration set, so that all validation analyses are via interpolation of the model.

TABLE 1

|  | Aromatic Content | Benzene Content |
| --- | --- | --- |
| $n_{cal}$ | 72 | 72 |
| SEC | 0.209 | 0.029 |
| $n_{val}$ | 77 | 77 |
| SEV | 0.399 | 0.032 |
| Weight Standard Error | 0.255 | 0.031 |
| $\sqrt{\dfrac{n_{cal}^2 SEC^2 + n_{val}^2 SEV^2}{n_{cal}^2 + n_{val}^2}}$ | | |
| Validation Bias | -0.003 | 0.000 |

For comparison, the Kennard-Stone method was used to select 72 calibration samples from the same set of 149 initial spectra. The results are shown in Table 2. The standard errors for the resultant model (weighted average of SEC and SEP is significantly poorer for the resultant model and the model biases are also larger. In the case of aromatics content, the Kennard-Stone based model has a statistically significant bias.

TABLE 2

|  | Aromatic Content | Benzene Content |
| --- | --- | --- |
| $n_{cal}$ | 72 | 72 |
| SEC | 0.451 | 0.050 |
| $n_{val}$ | 77 | 77 |
| SEV | 0.325 | 0.057 |

TABLE 2-continued

|  | Aromatic Content | Benzene Content |
| --- | --- | --- |
| Weight Standard Error | 0.389 | 0.054 |
| $\sqrt{\dfrac{n_{cal}^2 SEC^2 + n_{val}^2 SEV^2}{n_{cal}^2 + n_{val}^2}}$ | | |
| Validation Bias | -0.083 | -0.010 |

EXAMPLE 2

Optimization of an FT-MIR Multivariate Model for Estimation of Olefins Content and T50 and T90 Distillation Temperatures of Motor Gasolines The data set available for development of the multivariate model consists of 722 motor gasolines. FT-MIR spectra of motor gasolines were collected at 2 $cm^{-1}$ resolution over the 7000–400 $cm^{-1}$ spectral region. Olefins Contents for the gasolines are measured by ASTM D1319. The temperatures at which 10%, 50% and 90% of the gasoline distilled, T10, T50 and T90 respectively, were measured by ASTM D86. Additionally, motor octane number (ASTM D2700), research octane number (ASTM D2699), saturates content (ASTM D1319), specific gravity (ASTM D1298) and methyl t-butyl ether and oxygenate content (ASTM D4815) data were available for the 722 gasolines.

An initial division of the 722 gasolines into a calibration and validation set was made using the following method. The gasolines were sorted based on olefins content. The gasolines were numbered from 1 to 722, and numbers were divided by 20. If the remainder was 1, the gasoline was marked as a calibration sample. The gasolines were then sorted based on T50, and again numbered from 1 to 722, and the numbers were divided by 20. If the remainder was 1, the gasoline was marked as a calibration sample. This procedure was repeated in turn for T90, T10, MON, RON, sats content, specific gravity, MTBE content, and oxygen content. 299 samples were selected as calibration samples in this fashion.

An initial CPSA model was built using data in the 4750–3140 $cm^{-1}$ and the 2220–1630 $cm^{-1}$ regions. Orthogonalization to cubic and quadratic baseline polynomials is used in the two regions to minimize effects of baseline variation. Orthogonalization to water vapor spectra is used to minimize sensitivity to spectrometer purge variation. The initial model was based on 9 Constrained Principal Components. The model was used to analyze the 423 initial validation samples. The estimates for the validation samples showed a statistically significant bias for all three of the target properties (Table 3).

TABLE 3

|  | Olefins Content | T50 | T90 |
| --- | --- | --- | --- |
| $n_{cal}$ | 299 | 299 | 299 |
| SEC | 0.716 | 3.04 | 2.95 |
| $n_{val}$ | 423 | 423 | 423 |
| SEV | 0.766 | 2.88 | 2.93 |

TABLE 3-continued

|  | Olefins Content | T50 | T90 |
|---|---|---|---|
| Weight Standard Error | 0.750 | 2.93 | 2.94 |
| $\sqrt{\dfrac{n_{cal}^2 SEC^2 + n_{val}^2 SEV^2}{n_{cal}^2 + n_{val}^2}}$ | | | |
| Validation Bias | −0.162 | 1.234 | 2.026 |

A total of 21 of these initial samples were eliminated from the data base as being too unique to include in the models or having suspect property/component concentration data. The $V_{cal}$ and $V_{cal}$ scores for the remaining 701 samples were used in developing the optimized model.

For applying the Genetic Algorithm optimization, the X-Block data consisted of the $V_{cal}$ and $V_{cal}$ scores for the 701 samples, and the Y-Block data consisted of the olefins contents and the T50 and T90 distillation points. The number of calibration samples was constrained to fall between 278 and 417. Each generation consisted of 100 vectors, and up to 50 generations were calculated. A 95% probability of recombination and a 25% probability of mutation were used. The Genetic Algorithm optimization was initiated from a random initial population. The Genetic Algorithm was restarted 7 additional times using the best 25 vectors from the previous pass as one fourth of the initial population. The vector with the lowest Fitness Function was used to determine the division of sample spectra between calibration and validation sets. 279 calibration samples were identified. The results for the model build on the segregated sets are shown in Table 4. The model is unbiased for both olefins and distillation points, and the standard errors of calibration and validation are acceptable relative to the reproducibility of the corresponding reference methods (D1319 and D86 respectively). The maximum Mahalanobis distance for the validation set is less than that for the calibration set, so that all validation analyses are via interpolation of the model.

TABLE 4

|  | Olefins Content | T50 | T90 |
|---|---|---|---|
| $N_{cal}$ | 279 | 279 | 279 |
| SEC | 0.609 | 2.58 | 2.85 |
| $N_{val}$ | 422 | 422 | 422 |
| SEV | 0.720 | 2.94 | 3.05 |
| Weight Standard Error | 0.688 | 2.83 | 2.99 |
| $\sqrt{\dfrac{n_{cal}^2 SEC^2 + n_{val}^2 SEV^2}{n_{cal}^2 + n_{val}^2}}$ | | | |
| Validation Bias | −0.007 | −0.004 | 0.060 |

What is claimed is:

1. A method for optimizing the calibration of a multivariate model predicting chemical or physical properties of a sample based on multivariate analytical measurements of the sample, comprising:

a) obtaining multivariate analytical and property/composition data for a set of samples for calibrating and validation of said multivariate model;

b) dividing said multivariate analytical data or the data obtained by applying a mathematical function to said multivariate analytical data into initial calibration and validation subsets;

c) calculating a model with said calibration subset;

d) calculating a standard error of calibration, a standard error of validation, and a validation bias with said model;

e) determining whether samples in the validation set are outliers relative to the calibration set;

f) calculating a fitness function from said standard error of calibration, said standard error of validation, said validation bias, and the number of outliers; and g) interchanging the samples between said calibration and said validation subsets so as to identify a calibration and a validation subset that minimize said fitness function; and h) calibrating an optimized multivariate model using the calibration subset identified in step g).

2. A method of claim 1 wherein in step b), the multivariate analytical data is divided into calibration and validation subsets, in step c), a model is built using the calibration subset, and in step g), the multivariate analytical data is interchanged between the calibration and validation so as to minimize the fitness function.

3. A method of claim 1 wherein a model is built using the entire set of multivariate analytical data, in step b), the model variables are divided into calibration and validation subsets, in step c), a model is calculated using the model variables for the calibration subset, and in step g), the model variables are interchanged between the calibration and validation so as to minimize the fitness function.

4. A method of claim 1 wherein an existing model is used to analyze multivariate analytical data for an additional set of test samples, the independent model variables for the existing models are combined with those for the test samples, in step b), the combined independent model variables are subdivided into calibration and validation subsets, in step c), a model is calculated using the independent model variables for the calibration subset, and in step g), the model independent variables are interchanged between the calibration and validation so as to minimize the fitness function.

5. A method of claims 3 or 4 wherein the independent model variables are scores from a Principal Components Analysis of the multivariate analytical data.

6. A method of claims 3 or 4 wherein the independent model variables are scores from a Partial Least Squares Analysis of the multivariate analytical data.

7. A method of claims 3 or 4 wherein the independent model variables are scores from a Constrained Principal Spectra Analysis of the multivariate analytical data.

8. The method of claims 1, 2, 3, or 4 wherein said minimizing step is performed using a genetic algorithm.

9. The method of claim 8 wherein said genetic algorithm includes the steps of:

a) generating an initial set of parent vectors that indicate the subdivision of the samples into calibration and validation subsets;

b) calculating a fitness function for each of the parent vectors;

c) selecting the pairs of mating parent vectors from said initial set;

d) randomly determining if each pair of mating parent vectors will produce a new generation of children vectors by exchanging information, and if so, where along the parent vectors the exchange occurs;

e) randomly determining if the children vectors from d) will mutate, and if so, where along the child=en vectors the mutation occurs;

f) determining a fitness function for each vector in the set of the new generation of children vectors, and storing the lowest fitness functions; and g) repeating steps c) through f) such that the children vectors of step f) become the parent vectors of step c), until a predetermined stop criteria is satisfied.

10. The genetic algorithm of claim 8 wherein said stop criteria includes:

a) reaching a predetermined number of new generation of children vectors; and b) having no change in the fixed percentage of the lowest fitness functions for some fixed number of generations.

11. The method of claims 1, 2, 3, or 4 wherein said fitness function is $$FF = (1 + n_{outliers})\left(t + \sqrt{n_{cal}}\, SE\frac{C}{StdY} + \sqrt{n_{val}}\,\frac{SEV}{StdY}\right)$$

where $$t = \frac{\sqrt{n_{val}}\, VB}{SEV},$$

VB is average difference between $\hat{y}_{val}$ and $y_{val}$ $$SEC = \sqrt{\frac{(\hat{y}_{cal} - y_{cal})^t (\hat{y}_{cal} - y_{cal})}{n_{cal} - k}},$$

$$SEV = \sqrt{\frac{(\hat{y}_{val} - y_{val})^t (\hat{y}_{val} - y_{val})}{n_{val}}}$$

and $$StdY = \sqrt{\frac{y^t y}{n - 1}}.$$

12. A method of claims 1, 2, 3, or 4 wherein said fitness function is $$FF = (1 + n_{outliers})\left(t + \sqrt{n_{cal}}\,\frac{SEC}{R} + \sqrt{n_{val}}\,\frac{SEV}{R}\right)$$

where R is the reproducibility of the reference method used to determine the property/composition data in y.

13. A method for predicting a chemical or physical property using the model of claims 1, 2, 3, or 4.

14. The method of claims 1, 2, 3, or 4 wherein said multivariate data are infrared spectra.

15. The method of claims 1, 2, 3, or 4 wherein said multivariate data are Raman spectra.

16. The method of claims 1, 2, 3, or 4 wherein said multivariate data are gas chromatograms.

17. The method of claims 1, 2, 3 or 4 wherein said multivariate data are mass spectra.

18. The method of claim 13 wherein said composition data is olefins content.

19. The method of claim 13 wherein said composition data is aromatic content.

20. The method of claim 13 wherein said composition data is benzene content.

21. The method of claim 13 wherein said property data is research octane number.

22. The method of claim 13 wherein said property data is motor octane number.

23. The method of claim 13 wherein the property data is the temperature at which 10% of the sample distills.

24. The method of claim 13 wherein the property data is the temperature at which 50% of the sample distills.

25. The method of claim 13 wherein said property data is the temperature at which 90% of the sample distills.

26. The method of claim 13 wherein said property data is cetane number.

27. The method of claims 1, 2, 3, or 4 wherein the samples used in developing the multivariate model are motor gasolines.

28. The method of claims 1, 2, 3, or 4 wherein the samples used in developing the multivariate model are diesel fuels.

29. The method of claims 1, 2, 3, or 4 wherein the samples used in developing the multivariate model are jet fuels.

30. The method of claims 1, 2, 3, or 4 wherein the samples used in developing the multivariate model are feeds to a hydrocarbon conversion, separation or blending process.

31. The method of claims 1, 2, 3, or 4 wherein the samples used in developing the multivariate model are crude oils.

* * * * *